(12) United States Patent
Lai et al.

(10) Patent No.: US 8,377,902 B2
(45) Date of Patent: Feb. 19, 2013

(54) RNAI COMPOUND TARGETED TO THROMBOSPONDIN-1 AND APPLICATIONS THEREOF

(75) Inventors: Ming-Derg Lai, Tainan (TW); Shih-Shien Huang, Tainan (TW); Meng-Chi Yen, Tainan (TW); Chi-Chen Lin, Taichung (TW); Tzu-Yang Weng, Tainan (TW)

(73) Assignee: National Cheng Kung University (TW)

( * ) Notice: Subject to any disclaimer, the term of this patent is extended or adjusted under 35 U.S.C. 154(b) by 129 days.

(21) Appl. No.: 12/985,684

(22) Filed: Jan. 6, 2011

(65) Prior Publication Data

US 2011/0166199 A1 Jul. 7, 2011

(30) Foreign Application Priority Data

Jan. 7, 2010 (TW) ................................ 99100244 A

(51) Int. Cl.
*A61K 31/70* (2006.01)
*C07H 21/02* (2006.01)
*C07H 21/04* (2006.01)
*C12Q 1/68* (2006.01)

(52) U.S. Cl. ................. 514/44 A; 514/44 R; 435/320.1; 536/23.1; 536/24.1; 536/24.5

(58) Field of Classification Search ........................ None
See application file for complete search history.

(56) References Cited

U.S. PATENT DOCUMENTS

| 2004/0259247 A1* | 12/2004 | Tuschl et al. ................... 435/375 |
| 2008/0113351 A1* | 5/2008 | Naito et al. ........................ 435/6 |

OTHER PUBLICATIONS

Daniel et al. J. Am. Soc. Nephrol. vol. 13:5A, 2002.*
Brummelkamp et al. Science, vol. 296:550-553, 2002.*

* cited by examiner

*Primary Examiner* — Sean McGarry
(74) *Attorney, Agent, or Firm* — Bacon & Thomas, PLLC

(57) ABSTRACT

The present invention relates to an RNAi compound and an expression plasmid for inhibiting expression of Thrombospondin-1, which comprises a target sequence selected from Thrombospondin-1 gene. The present invention also related to a pharmaceutical composition comprising the RNAi compound and applications thereof. The RNAi compound can reduce the expression of Thrombospondin-1 to activate immune responses. In addition, the present invention also disclosed that an RNAi compound targeted to Thrombospondin-1 gene can delay tumor progression.

6 Claims, 3 Drawing Sheets

(A)

(B)

SEQUENCE LISTING

```
<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Synthetic DNA

<400> SEQUENCE: 1
gccagaactc ggttaccat                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic DNA

<400> SEQUENCE: 2
ccaacaaaca ggtgtgcaa                                                19

<210> SEQ ID NO 3
<211> LENGTH: 19
<212> TYPE: DNA
<213> ORGANISM: Artificial Sequence
<220> FEATURE:
<223> OTHER INFORMATION: Synthetic DNA

<400> SEQUENCE: 3
gcaactacct gggtcacta                                                19

<210> SEQ ID NO 4
<211> LENGTH: 19
<212> TYPE: DNA
<213> ORGANISM: Artificial Sequence
<220> FEATURE:
<223> OTHER INFORMATION: Synthetic DNA

<400> SEQUENCE: 4
ggtccaacag tcgaactct                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetic DNA

<400> SEQUENCE: 5
```

-continued atggtaaccg agttctggc                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic DNA

<400> SEQUENCE: 6
ttgcacacct gtttgttgg                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic DNA

<400> SEQUENCE: 7
tagtgaccca ggtagttgc                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic DNA

<400> SEQUENCE: 8
agagttcgac tgttggacc                                                19

<210> SEQ ID NO 9
<211> LENGTH: 9
<212> TYPE: DNA
<213> ORGANISM: Artificial Sequence
<220> FEATURE:
<223> OTHER INFORMATION: Synthetic DNA

<400> SEQUENCE: 9 ttcaagaga                                                            9

<210> SEQ ID NO 10
<211> LENGTH: 1869
<212> TYPE: DNA
<213> ORGANISM: Human cytomegalovirus

<400> SEQUENCE: 10
acccaagtgt gcaccggcac agacatgaag ctgcggctcc ctgccagtcc cgagacccac      60
ctggacatgc tccgccacct ctaccagggc tgccaggtgg tgcagggaaa cctggaactc     120
acctacctgc ccaccaatgc cagcctgtcc ttcctgcagg atatccagga ggtgcagggc     180
tacgtgctca tcgctcacaa ccaagtgagg caggtcccac tgcagaggct gcggattgtg     240
cgaggcaccc agctctttga ggacaactat gccctggccg tgctagacaa tggagacccg     300
ctgaacaata ccacccctgt cacagggggcc tccccaggag gcctgcggga gctgcagctt     360
cgaagcctca cagagatctt gaaaggaggg gtcttgatcc agcggaaccc ccagctctgc     420
taccaggaca cgattttgtg gaaggacatc ttccacaaga caaccagct ggctctcaca     480 ctgatagaca ccaaccgctc tcgggcctgc caccccctgtt ctccgatgtg taagggctcc     540
cgctgctggg gagagagttc tgaggattgt cagagcctga cgcgcactgt ctgtgccggt     600
ggctgtgccc gctgcaaggg gccactgccc actgactgct gccatgagca gtgtgctgcc     660

```
ggctgcacgg gccccaagca ctctgactgc ctggcctgcc tccacttcaa ccacagtggc    720
atctgtgagc tgcactgccc agccctggtc acctacaaca cagacacgtt tgagtccatg    780
cccaatcccg agggccggta tacattcggc gccagctgtg tgactgcctg tcctacaac    840
taccttcta cggacgtggg atcctgcacc ctcgtctgcc cctgcacaa ccaagaggtg    900
acagcagagg atggaacaca gcggtgtgag aagtgcagca gccctgtgc ccgagtgtgc    960
tatggtctgg gcatggagca cttgcgagag gtgagggcag ttaccagtgc caatatccag   1020
gagtttgctg gctgcaagaa gatctttggg agcctggcat ttctgccgga gagctttgat   1080
ggggacccag cctccaacac tgccccgctc cagccagagc agctccaagt gtttgagact   1140
ctggaagaga tcacaggtta cctatacatc tcagcatggc cggacagcct gcctgacctc   1200
agcgtcttcc agaacctgca gtaatccgg ggacgaattc tgcacaatgg cgcctactcg   1260
ctgaccctgc aagggctggg catcagctgg ctggggctgc gctcactgag ggaactgggc   1320
agtggactgg ccctcatcca ccataacacc cacctctgct tcgtgcacac ggtgccctgg   1380
gaccagctct ttcggaaccc gcaccaagct ctgctccaca ctgccaaccg gccagaggac   1440
gagtgtgtgg gcgagggcct ggcctgccac cagctgtgcg cccgagggca ctgctggggt   1500
ccagggccca cccagtgtgt caactgcagc cagttccttc ggggccagga gtgcgtggag   1560
gaatgccgag tactgcaggg gctccccagg gagtatgtga atgccaggca ctgtttgccg   1620
tgccaccctg agtgtcagcc ccagaatggc tcagtgacct gttttggacc ggaggctgac   1680
cagtgtgtgg cctgtgccca ctataaggac cctcccttct gcgtggcccg ctgccccagc   1740
ggtgtgaaac ctgacctctc ctacatgccc atctggaagt ttccagatga ggagggcgca   1800
tgccagcctt gccccatcaa ctgcacccac tcctgtgtgg acctggatga caagggctgc   1860
cccgccgag                                                           1869

<210> SEQ ID NO 11
<211> LENGTH: 1560
<212> TYPE: DNA
<213> ORGANISM: human thrombospondin 1

<400> SEQUENCE: 11
aaagtgacgg aagagaacag agagctggtc agtgagctga agcggcctcc cctctgcttt     60
cacaatggag tccagtacaa gaacaacgag gagtggactg tagacagttg cacagagtgt    120
cactgccaga actcggttac catctgcaaa aaggtgtcct gtcccatcat gccctgctcc    180
aacgccacag ttcctgatgg tgaatgctgc ccacggtgct ggcccagcga ctctgctgac    240
gatggctggt ctccctggtc tgagtggacc tcctgctctg ccacatgtgg caatggaatt    300
cagcaacgtg gtcgttcctg tgacagcctc aacaacagat gcgagggctc ttcggtacag    360
acaaggacct gccacattca ggagtgtgac aaaagattta acaggatgg tggctggagt    420
cactggtctc catggtcgtc ctgttctgtg acctgtggtg acgtgtgat cacaaggatc    480
cggctctgca actccccag ccccagatg aacgggaagc cctgtgaagg tgaagcccgg    540
gagaccaaag cctgcaagaa agacgcctgc ccaattaatg gaggctgggg tccctggtca    600
ccatgggaca tctgctctgt cacctgtgga ggaggagtgc agagacgcag ccgactctgt    660
aacaacccca caccccagtt tggaggcaaa gactgtgttg gcgatgtgac agaaaatcaa    720
gtttgcaaca gcaggactg cccaattgat ggatgcctgt ccaatcctg ctttgctggt    780
gccaagtgta ctagctaccc tgatggtagc tggaaatgtg gtgcgtgtcc tcctggctac    840
agtggaaatg gcatccagtg caaagacgtc gatgagtgca aagaagtgcc tgatgcttgc    900
```

-continued

```
ttcaatcaca acggagaaca tcggtgcaag aacacagatc ctggctacaa ctgcctgccc      960
tgcccaccac gattcactgg ctcacagccc ttcggccgag gtgtcgaaca tgccatggcc     1020
aacaaacagg tgtgcaaacc gcgaaacccc tgcacggacg ggacgcatga ctgcaacaag     1080
aacgctaagt gcaactacct gggtcactac agtgacccca tgtaccgctg tgagtgcaag     1140
cccggctatg caggcaatgg catcatctgc ggagaggaca cagacctgga cggctggcct     1200
aatgaaaacc tggtgtgtgt ggccaacgca acctaccact gcaaaaagga caactgcccc     1260
aaccttccca actcggggca ggaagactat gacaaggacg ggattggcga tgcctgcgat     1320
gatgacgatg acaacgacaa gatccccgat gacagggaca actgtccatt ccattacaac     1380
ccagcccagt atgactatga cagagatgat gtgggagacc gctgtgacaa ctgcccctac     1440
aaccacaacc ctgaccaagc agacacagac aaaaacgggg agggcgatgc ctgtgctgtg     1500
gacatcgatg gagatggaat cctcaatgaa cgagacaact gccagtacgt ttacaacgtg     1560
```

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
tatgtgccta atgccaacca        20

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
cgctgaagtc cacagcatta        20

US 8,377,902 B2

RNAI COMPOUND TARGETED TO THROMBOSPONDIN-1 AND APPLICATIONS THEREOF

BACKGROUND OF THE INVENTION

1. Field of the Invention

The present invention relates to an RNAi compound and an expression plasmid for inhibiting expression of Thrombospondin-1, a pharmaceutical composition containing the RNAi compound, and a method of treating cancer using the RNAi compound.

2. Description of Related Art

The Thrombospondin protein family consists of thrombospondin 1-5. Thrombospondin-1 (TSP-1) is widely distributed in normal tissue, including heart, lung, liver, spleen and stomach. TSP-1 is mainly secreted by platelets and dendritic cells (DCs), and has multiple biological functions including inhibition of angiogenesis, apoptosis, and activation of transforming growth factor beta (TGF-β) and immune regulation.

Dendritic cells play a major role on activating adoptive immune responses and express TSP-1 during its inactivation. Then, the expressed TSP-1 converts the TGF-β from a latent state into an activated state. The TGF-β is a regulation factor of the immune system, and converts effect T cells into regulatory T cells to suppress immune responses. TSP-1 also interacts with CD47 on T cells to enhance the apoptosis of T cells and the formation of regulatory T cells, and inhibit the immune responses resulting from inflammation. Hence, the immune responses can be improved if the expression of TSP-1 is inhibited.

Conventional immune therapy is accomplished by inducing an immune response with abundant tumor-associated antigens. However, abundant inhibitory cytokines are also generated, which further induce the proliferation of regulatory T cells of patients. The proliferation of regulatory T cells may suppress immune responses. In addition, the tumor-associated antigens are autoantigens, which may cause autoimmune diseases.

In addition, it has been reported that CD25 monoclonal antibodies can be used to suppress regulatory T cells to improve the effect of immune therapy. However, the production cost of monoclonal antibodies is high, and the monoclonal antibodies may cause undesired systematic suppression.

Therefore, it is desirable to provide a drug or an improved method to treat cancer through immune therapy.

SUMMARY OF THE INVENTION

The object of the present invention is to provide an RNAi compound or an shRNA expression plasmid, which can encode an siRNA to inhibit expression of Thrombospondin-1 (TSP-1) through an RNAi pathway. TSP-1 regulates immune responses through the activation of functional domain of TGF-β. When the shRNA expression plasmid is used to inhibit the expression of TSP-1, Dicer cleaves shRNA expression plasmid in cells to form an siRNA, which is a polynucleotide with high specificity. The storage of the RNAi compound or the expression plasmid of the present invention is very simple. Furthermore, the manufacturing process of the RNAi compound or the expression plasmid of the present invention is much simpler than that of protein antigens, so the production cost can be greatly decreased. The RNAi compound or siRNA generated from the expression plasmid of the present invention can suppress the expression of the TSP-1 to activate immune responses. If the RNAi compound or siRNA generated from the expression plasmid of the present invention can be delivered into dendritic cells, the immune responses are much more obvious.

Another object of the present invention is to provide a pharmaceutical composition, which comprises the aforementioned RNAi compound or the aforementioned expression plasmid, and pharmaceutical composition.

A further object of the present invention is to provide a method of treating cancer, which comprises a step of administering a therapeutically effective amount of the aforementioned pharmaceutical composition.

Another further object of the present invention is to provide a use of the aforementioned RNAi compound or the aforementioned plasmid to manufacture a DNA vaccine.

To achieve the object, the RNAi compound for inhibiting expression of TSP-1 of the present invention comprises: a target sequence selected from TSP-1 gene.

The expression plasmid for inhibiting expression of TSP-1 of the present invention comprises: a target sequence selected from TSP-1 gene; and a reverse complement of the target sequence. Herein, the expression plasmid is an shRNA expression plasmid, and the target sequence encodes an siRNA targeted to TSP-1 gene. In addition, the expression plasmid may further comprise a hairpin sequence locating between the target sequence and the reverse complement.

In addition, the pharmaceutical composition of the present invention comprises: an RNAi compound, and a pharmaceutically acceptable carrier. Herein, the RNAi compound comprises a target sequence selected from TSP-1 gene.

Furthermore, the method of treating cancer of the present invention comprises a step of administering a therapeutically effective amount of the aforementioned pharmaceutical composition to a patient in need.

According to the RNAi compound and the expression plasmid of the present invention, the target sequence can be any continuous sequence selected from an encoding region corresponding to nucleotides 1 to 3516 of TSP-1 gene. Preferably, the target sequence comprises 20-25 nucleotides selected from an encoding region corresponding to nucleotides 1 to 3516 of TSP-1 gene. More preferably, the target sequence is SEQ ID NO: 1, SEQ ID NO: 2, or SEQ ID NO: 3.

In addition, according to the RNAi compound and the pharmaceutical composition containing the RNAi compound of the present invention, the RNAi compound is an isolated siRNA, or an shRNA expression plasmid for encoding a siRNA. Herein, the siRNA corresponds to the target sequence. Furthermore, the shRNA expression plasmid comprises the target sequence, and a reverse complement of the target sequence, preferably.

According to the present invention, the RNAi compound or the expression plasmid further comprises: an Her2/neu gene, wherein the Her2/neu gene connects to the target sequence. Preferably, the sequence of the Her2/neu gene corresponds to nucleotides 21 to 653 of human neu gene. More preferably, the sequence of the Her2/neu gene is SEQ ID NO: 10.

In addition, according to the pharmaceutical composition and the method of the present invention, the pharmaceutically acceptable carrier is selected from a group consisting of saline, phosphate buffered saline (PBS), and sterile water.

Furthermore, according to the method of the present invention, the pharmaceutical composition is administered through a gene gun or an intramuscular injection.

In conclusion, the present invention provides an RNAi compound and an expression plasmid for inhibiting expression of TSP-1, a pharmaceutical composition containing the same, and a method of treating cancer by using the same. Compared to protein antigens conventionally used in vaccines, the RNAi compound and the expression plasmid of the present invention comprises the advantages of high specificity, fewer side-effects, easy preparation and storage, low production cost, and easy use. The amount of regulatory T cells can be decreased and the generation of cytokines can be suppressed by injection of the RNAi compound once a week. In addition, the survival time of patients can be increased, and the growth of tumor cells can be delayed.

In addition, the RNAi compound and the expression plasmid of the present invention can be used to treat cancer when it is used alone. When the RNAi compound and the expression plasmid is used with other DNA vaccines, the efficiency of DNA vaccines can be greatly increased.

DETAILED DESCRIPTION OF THE PREFERRED EMBODIMENT

Figure 1:
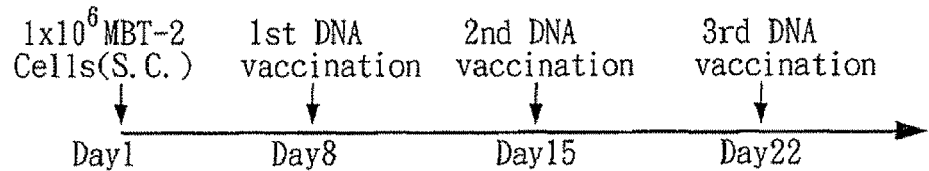
FIG. 1A is an in vivo experimental process using an shRNA-1 expression plasmid of the present invention.
FIG. 1B is an in vivo experimental result showing tumor volumes in mice.
FIG. 1C is an in vivo experimental result showing the survival percentages of mice, wherein "*" represents $p<0.05$, "" represents $p<0.01$, and "*" represents $p<0.005$.
Figure 1:
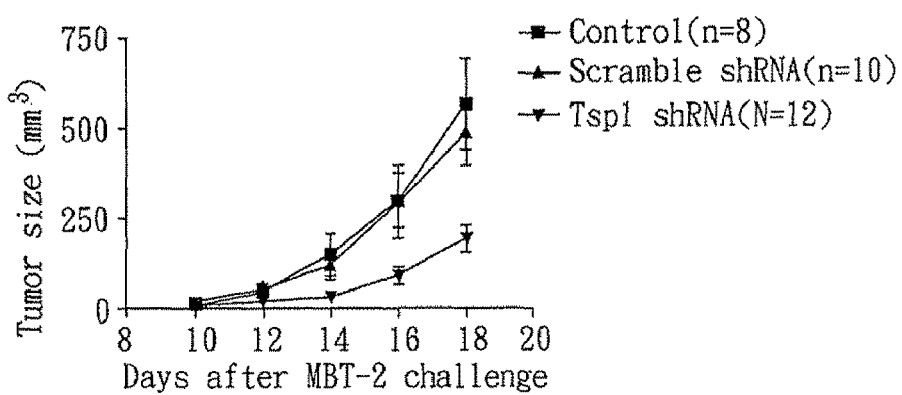
Figure 1:
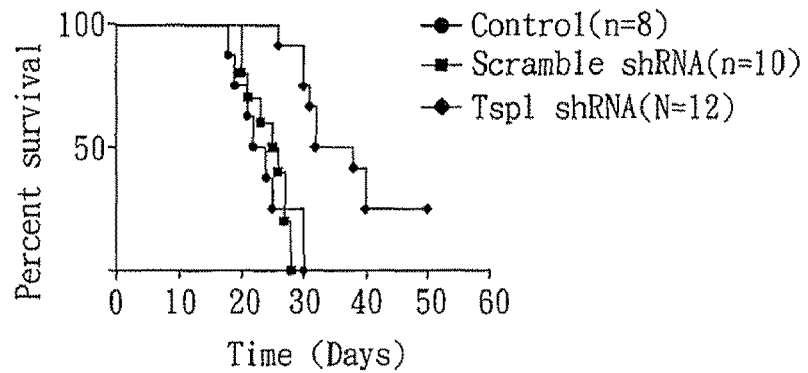

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Embodiment

Cell Culture

In the present embodiment, mouse bladder tumor cells (MBT-2) and African green monkey kidney fibroblast cells (Cos 7) were cultured in DMEM medium containing 10% of fetal calf serum (FBS) and 1% of Penicillin-Streptomycin.

Animal Model

In the present embodiment, female C3H/HeN mice (4-6 weeks of age) were used in the in vivo experiment.

Plasmid Construction and Vaccine Preparation

The target sequences shown in the following Table 1 (i.e. SEQ ID NOs: 1-3) and pHsU6 vectors were used to construct shRNA expression plasmids of TSP-1. The target sequences were used as forward oligonucleotides, complements of the target sequences were used as reverse oligonucleotides (i.e. SEQ ID NOs: 5-7), and a hairpin sequence TTCAAGAGA (i.e. SEQ ID NO: 9) was inserted into the target sequences and the complements. Then, shRNA sequences containing the forward oligonucleotides, the hairpin sequence, and the reverse oligonucleotides were inserted into pHsU6 plasmid between the restriction sites of ClaI and HindIII. The obtained pHsU6 shRNA expression plasmids were named as follow: pHsU6 Tsp-1 shRNA-1, pHsU6 Tsp-1 shRNA-2, and pHsU6 Tsp-1 shRNA-3.

TABLE 1

| Plasmid | Forward/reverse oligonucleotides | |
|---|---|---|
| Tsp-1 shRNA-1 | 5'-GCCAGAACTCGGTTACCAT-3' | SEQ ID NO: 1 |
| | 5'-ATGGTAACCGAGTTCTGGC-3' | SEQ ID NO: 5 |
| Tsp-1 shRNA-2 | 5'-CCAACAAACAGGTGTGCAA-3' | SEQ ID NO: 2 |
| | 5'-TTGCACACCTGTTTGTTGG-3' | SEQ ID NO: 6 |
| Tsp-1 shRNA-3 | 5'-GCAACTACCTGGGTCACTA-3' | SEQ ID NO: 3 |
| | 5'-TAGTGACCCAGGTAGTTGC-3' | SEQ ID NO: 7 |
| Tsp-1 shRNA-1 scrambled shRNA | 5'-GGTCCAACAGTCGAACTCT-3' | SEQ ID NO: 4 |
| | 5'-AGAGTTCGACTGTTGGACC-3' | SEQ ID NO: 8 |

In addition, U6 promoter in pHsU6 Tsp-1 shRNA-1 plasmid and Tsp-1 shRNA-1 gene were inserted into human-cyto-N'-neu plasmid between the restriction sites of AvrII and EcoRI, to obtain a fusion plasmid of human-cyto-N'-neu-Tsp-1 shRNA-1. Herein, the human-cyto-N'-neu plasmid is a plasmid, which contains an encoding region corresponding to nucleotides 21-653 (SEQ ID NO: 10) inserted into pRC/CMV vector (Invitrogen) between NotI and HindIII.

Tsp-1 shRNA-1 scrambled shRNA was prepared by the same method for preparing Tsp-1 shRNA-1, and used as a negative control. The sequences of scrambled shRNA were generated with an siRNA Wizard™ program developed by InvivoGen (http://www.sirnawizard.com/). The sequence of TSP-1 shRNA-1 was used as a template, and re-composed to obtain a scrambled sequence. The obtained sequence of the forward nucleotides and the reverse nucleotides of the scrambled shRNA were SEQ ID NO: 4 and SEQ ID NO: 8 respectively, as shown in Table 1.

In addition, the truncated form of Tsp-1 gene (i.e. an encoding region corresponding to nucleotides 1083-2642 (SEQ ID NO: 11)) was inserted into HA6L vector, which was pcDNA3 (Invitrogen) vector connecting with an N-terminal of HA peptide, and then an HA6L Tsp-1 plasmid was obtained. This obtained HA6L Tsp-1 plasmid was used to generate Tsp-1 protein for the following in vitro experiments.

The aforementioned plasmids were purified with Plasmid Mega Kit without endotoxin (QIAGEN). The purified shRNA expression plasmid can be used as DNA vaccines in the following experiments.

Tsp-1 RNAi Compound Inhibits Expression of TSP-1 Protein In Vitro.

The transfection was performed with Lipofectamine™ 2000 (Invitrogen). First, DNA was provided, which contained 1.8 μg shRNA and 0.2 μg target plasmid. The DNA was mixed with Lipofectamine in a ratio of 1:2 at room temperature according to the protocol. Then, cells seeded in a plate ($3\times10^5$/well) were transfected with the mixture. After 24 hrs, proteins were collected with an RIPA buffer.

The collected proteins were analyzed with a Western Blot Analysis generally used in the art. The primary antibody (1:5000 dilution) was a mouse anti-HA monoclonal antibody (3F10, Roche), and the secondary antibody (1:5000 dilution) was a goat anti-mouse IgG (Chemicon). The inner control of the Western Blot Analysis was actin. The primary antibody for actin (1:5000 dilution) was an actin antibody (MAB1510, Roche), and the secondary antibody (1:5000 dilution) was an anti-mouse IgG (Cell signally).

The results of the Western Blot Analysis showed that abundant HA Tsp-1 fusion protein was generated when HA6L Tsp-1 and pHsU6 plasmid was co-transfected in a ratio of 1:9 and the total FNA amount was 2 mg. However, when HA6L Tsp-1 and pHsU6 Tsp-1 shRNA-1 plasmid were co-transfected, the expression of Tsp-1 protein was inhibited by Tsp-1 shRNA-1 plasmid.

Tsp-1 RNAi Compound Inhibits Expression of TSP-1 Protein In Vivo.

Tsp-1 shRNA expression plasmid can inhibit expression of Tsp-1 in dendritic cells (DCs) inside lymph nodes in vivo.

Saline (control), or saline contained 10 μg of pHsU6 TSP-1 scrambled shRNA-1 plasmid or pHsU6 TSP-1 shRNA-1 plasmid was injected into mouse abdomens with Low-pressure Gene Delivery System (GDS-80, WEALTEC) at 50 psi. After 48 hrs, the mice were sacrificed to access inguinal lymph nodes. The lymph nodes were lysed, and $CD11c^+$ dendritic cells were separated out with CD11c (N418) Microbeads (Miltenyi Biotec). Then, RNAs of $CD11c^+$ dendritic cells were obtained with TRIZOL kit (Invitrogen Life Technologies), and the RNAs were reverse-transcribed by MMLV reverse transcriptase (Promega) to obtain cDNA. Finally, the expression amount of Tsp-1 and HPRT (hypoxanthine-guanine phosphoribosyltransferase) as an inner control was analyzed with RT-PCR. The primers for Tsp-1 and HPRT are listed as follow.

```
Primer for Tsp-1
5'-TATGTGCCTAATGCCAACCA-3'    (SEQ ID NO: 12)

5'-CGCTGAAGTCCACAGCATTA-3'    (SEQ ID NO: 13)
```

The results show that the expression of Tsp-1 in dendritic cells (DCs) inside mouse lymph nodes treated with pHsU6 TSP-1 shRNA-1 plasmid of the present invention was much lower than that treated with saline and pHsU6 TSP-1 scrambled shRNA-1 plasmid. Hence, the TSP-1 shRNA-1 plasmid of the present invention can inhibit expression of mRNA of Tsp-1, but the pHsU6 TSP-1 scrambled shRNA-1 plasmid having similar composition cannot inhibit expression of mRNA of Tsp-1.

Evaluation of the Effect of Treating MBT-2 Tumor Cells with RNAi Compounds

Mouse bladder tumor cell line MBT-2 with a concentration of $5 \times 10^6$ cells/ml PBS was injected into female C3H/HeN mice (4-6 weeks of age) through subcutaneously injection (s.c.), and $1 \times 10^6$ tumor cells were planted into dorsum of the mice to perform tumor challenge. The day of plating tumor cells was Day 1. At Days 8, 15 and 22, the mice were treated with 10 μg of pHsU6 TSP-1 scrambled shRNA-1 plasmid or pHsU6 TSP-1 shRNA-1 plasmid in PBS buffer through a Low-pressure Gene Delivery System (GDS-80, WEALTEC) at 50 psi. The schematic outline of the experimental design is shown in FIG. 1A. The mice treated with saline served as a control.

After MBT-2 tumor cells were injected, the nodule on the dorsum of the mice was measured and the survival percentage was recorded at specific time points. The equation for calculating the nodule is: $V = a^2 \times b \times 0.5236$, wherein V is the volume of tumor, a is the width of tumor, and b is the length of tumor.

As shown in FIG. 1B, the tumor size on the dorsum of the mice was smaller than that of the control, and the treating effect of pHsU6 TSP-1 shRNA-1 plasmid was better than that of the control. In addition, the survival time of the mice treated with pHsU6 TSP-1 shRNA-1 plasmid was longer than that of the control.

The Expression of Tsp-1 can be Inhibited by shRNA Plasmid with Different Tsp-1 Fragments In Vitro and In Vivo.

In order to confirm that the shRNA plasmid of the present invention can specifically inhibit the expression of Tsp-1, TSP-1 shRNA-1 plasmid and shRNA plasmids having two different target sequences were used to test the effect of the inhibition on Tsp-1.

The transfection and the Western Blot Analysis were performed as illustrated above, except that the shRNA plasmid were pHsU6 Tsp-1-shRNA-1, pHsU6 Tsp-1 shRNA-2, pHsU6 Tsp-1 shRNA-3, and pHsU6 TSP-1 scrambled shRNA plasmids.

The result of the Western Blot Analysis shows that abundant HA Tsp-1 fusion protein was generated when HA6L Tsp-1 and pHsU6 plasmid was co-transfected. However, when HA6L Tsp-1 was co-transfected with pHsU6 Tsp-1 shRNA-1 plasmid, pHsU6 Tsp-1 shRNA-2 plasmid, and pHsU6 Tsp-1 shRNA-3 plasmid, the expression of the HA Tsp-1 fusion protein was inhibited. However, the pHsU6 Tsp-1 scrambled shRNA-1 plasmid, which has similar composition to that of pHsU6 Tsp-1 shRNA-1 plasmid, cannot inhibit the expression of Tsp-1 protein.

In addition, the evaluation of the effect of treating MBT-2 tumor cells, which includes measurement of tumor sizes and record of survival time, was performed as illustrated above, except that the shRNA plasmid were pHsU6 Tsp-1 shRNA-1, pHsU6 Tsp-1 shRNA-2, and pHsU6 Tsp-1 shRNA-3 plasmids. The results are shown in FIGS. 2A and 2B.

Figure 2:
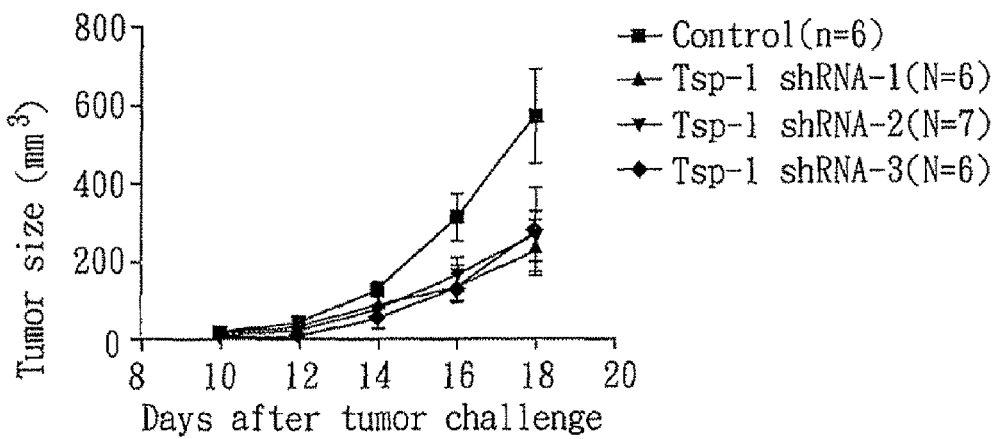
FIG. 2A is an in vivo experimental result showing tumor volumes in mice by administering shRNA-1, shRNA-2, and shRNA-3 of the present invention, wherein "*" represents $p<0.05$, "" represents $p<0.01$, and "*" represents $p<0.005$.
FIG. 2B is an in vivo experimental result showing the survival percentages of mice by administering shRNA-1, shRNA-2, and shRNA-3 of the present invention.
Figure 2:
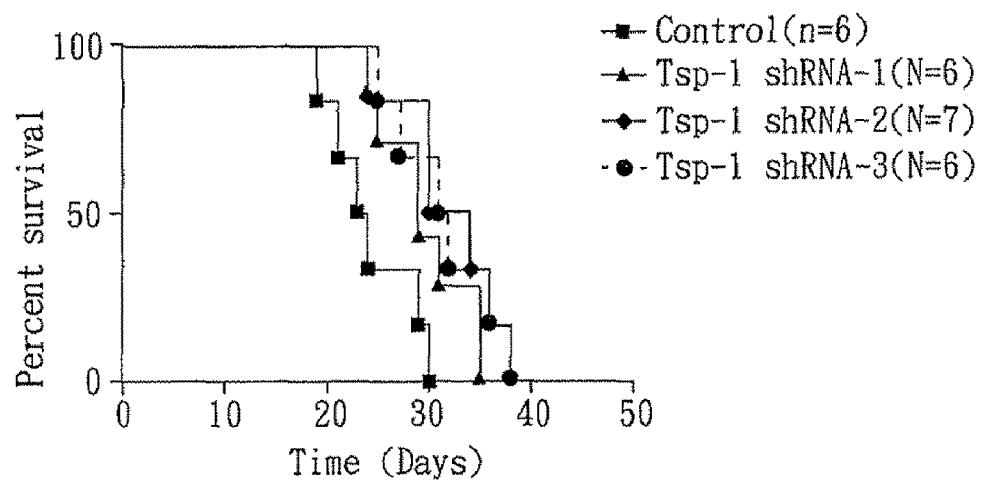

As shown in FIG. 2A, the growth of the tumor cells on the dorsum of the mice can be inhibited by administering pHsU6 Tsp-1 shRNA-1, pHsU6 Tsp-1 shRNA-2, and pHsU6 Tsp-1 shRNA-3 plasmids of the present invention, compared to that by administering saline (i.e. control). The results of the inhibition on tumor cells are consistent with the results of the inhibition on the expression of Tsp-1 protein.

As shown in FIG. 2B, the survival time of the mice administered with pHsU6 Tsp-1 shRNA-1, pHsU6 Tsp-1 shRNA-2, and pHsU6 Tsp-1 shRNA-3 plasmids of the present invention were increased, compared to that administered with saline (i.e. control).

The Effect of Treating Cancer can be Improved by Administering Tsp-1 shRNA-1 Fused with Tumor-Associated Antigen Her2/neu.

The evaluation of the effect of treating MBT-2 tumor cells, which includes measurement of tumor sizes and record of survival time, was performed as illustrated above, except that shRNA plasmids are pHsU6 Tsp-1 shRNA-1 plasmid, human-cyto-N'-neu plasmid, and human-cyto-N'-neu-Tsp-1 shRNA-1 plasmid. The results are shown in FIGS. 3A and 3B.

Figure 3:
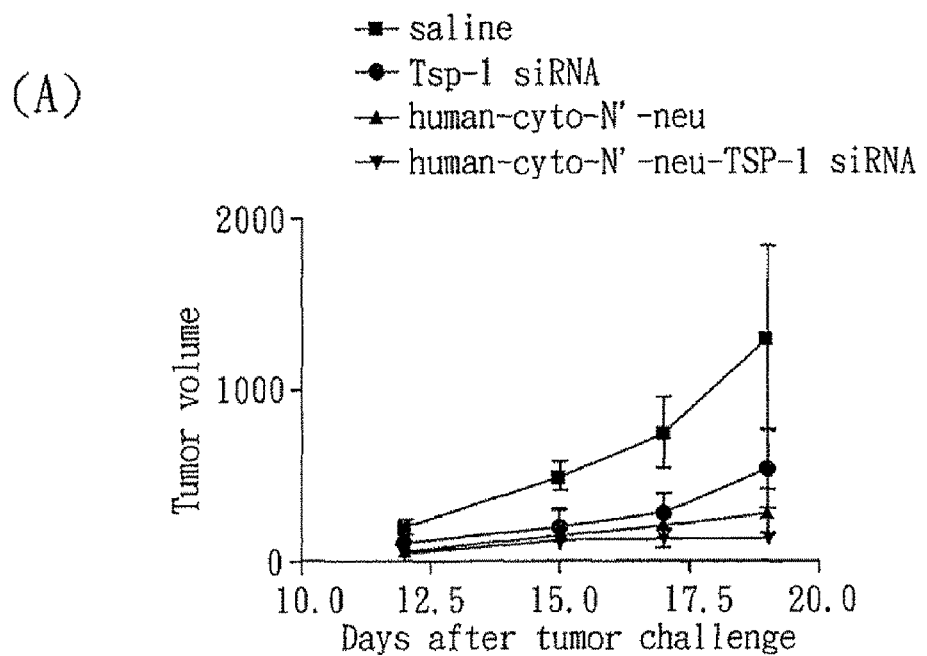
FIG. 3A is an in vivo experimental result showing tumor volumes in mice by administering shRNA-1 of the present invention combined with a tumor antigen vaccine.
FIG. 3B is an in vivo experimental result showing the survival percentages of mice by administering shRNA-1 of the present invention combined with a tumor antigen vaccine, wherein "*" represents $p<0.05$, "" represents $p<0.01$, and "*" represents $p<0.005$.
Figure 3:
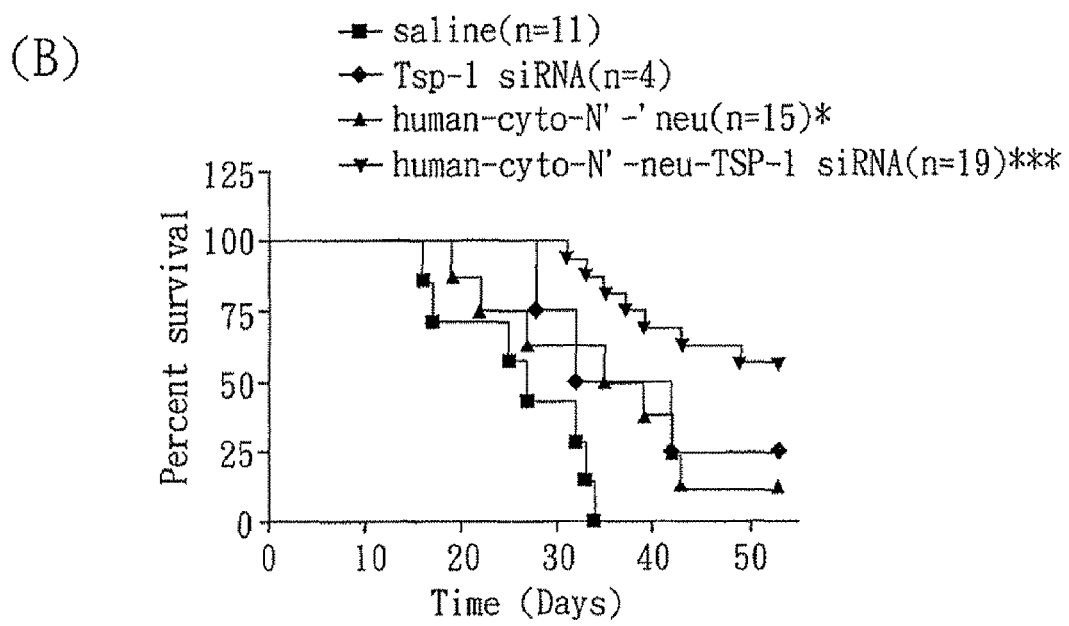

As shown in FIG. 3A, the growth of the tumor cells on the dorsum of the mice can be inhibited by administering pHsU6 Tsp-1 shRNA-1 plasmid of the present invention or human-cyto-N'-neu plasmid (i.e. Her2/neu DNA vaccine), compared to that by administering saline (i.e. control). In addition, human-cyto-N'-neu-Tsp-1 shRNA-1 plasmid (i.e. fusion DNA vaccine) showed better inhibition effect on the growth of the tumor cells.

As shown in FIG. 3B, the survival time of the mice administered with pHsU6 Tsp-1 shRNA-1 plasmid or human-cyto-N'-neu plasmid (i.e. Her2/neu DNA vaccine) were increased, compared to that administered with saline (i.e. control). In addition, human-cyto-N'-neu-Tsp-1 shRNA-1 plasmid (i.e. fusion DNA vaccine) showed better effect on the increase of the survival time.

In conclusion, according to the in vivo experiment, the expression of Tsp-1 in dendritic cells (DCs) inside lymph nodes can be inhibited through administering the Tsp-1 shRNA plasmid of the present invention with a gene gun. In addition, according to the experiment on mice with bladder tumor cells, the Tsp-1 shRNA plasmid with specificity of the present invention can significantly inhibit the growth of tumor cells, and extend the survival time of mice.

In addition, the Tsp-1 shRNA plasmids with different Tsp-1 fragments have similar therapeutic effects. Hence, the Tsp-1 shRNA plasmids of the present invention can specifically inhibit the expression of Tsp-1 protein.

When the Tsp-1 shRNA is fused with tumor-associated antigen Her2/neu gene, the effect of DNA vaccine can be further improved. Hence, the Tsp-1 shRNA indeed can improve anticancer immune responses. Therefore, the siRNA compound with Tsp-1 gene can trigger the anticancer immune responses, and can be used as DNA vaccine or be used with other immune therapies.

Although the present invention has been explained in relation to its preferred embodiment, it is to be understood that many other possible modifications and variations can be made without departing from the scope of the invention as hereinafter claimed.

What is claimed is:

1. An expression plasmid for RNAi inhibition of Thrombospondin-1 expression, comprising:
   a target sequence; and
   a reverse complement of the target sequence,
   wherein:
   the target sequence is selected from the group consisting of SEQ ID NO: 1, SEQ ID NO: 2, and SEQ ID NO: 3;
   the expression plasmid directs the synthesis of an siRNA or shRNA that targets the human Thrombospondin-1 gene in human cells; and
   the expression plasmid further comprises the Her2/neu gene.

2. The expression plasmid of claim 1, wherein the Her2/neu gene comprises SEQ ID NO: 10.

3. A pharmaceutical composition, comprising:
   the expression plasmid of claim 1; and
   a pharmaceutically acceptable carrier.

4. The pharmaceutical composition of claim 3, wherein the pharmaceutically acceptable carrier is selected from the group consisting of saline, phosphate buffered saline (PBS), and sterile water.

5. The expression plasmid of claim 1, further comprising a hairpin sequence.

6. The expression plasmid of claim 5, wherein the hairpin sequence is SEQ ID NO: 9.

* * * * *